United States Patent [19]

Sato et al.

[11] Patent Number: 4,825,862

[45] Date of Patent: * May 2, 1989

[54] PRESSURE REGULATOR FOR CUFF OF ENDOTRACHEAL TUBE WITH SUPERPOSITION OF VENTILATING PRESSURE VARIATION

[75] Inventors: Toru Sato; Toshihisa Hasegawa, both of Yonago, Japan

[73] Assignee: Tottori University, Tottori, Japan

[*] Notice: The portion of the term of this patent subsequent to Sep. 13, 2005 has been disclaimed.

[21] Appl. No.: 8,957

[22] Filed: Jan. 30, 1987

[30] Foreign Application Priority Data

Feb. 14, 1986 [JP] Japan .................................. 61-29098

[51] Int. Cl.[4] ............................................. A61M 16/00
[52] U.S. Cl. ............................. 128/207.15; 128/207.16
[58] Field of Search ....................... 128/207.15, 207.16, 128/207.14, 205.24; 604/96-99

[56] References Cited

U.S. PATENT DOCUMENTS

| | | | |
|---|---|---|---|
| 3,529,596 | 9/1970 | Garner | 128/207.15 |
| 3,931,822 | 1/1976 | Marici | 128/207.15 |
| 4,178,938 | 12/1979 | Au | 128/207.15 |
| 4,285,340 | 8/1981 | Gezari et al. | 128/207.15 |
| 4,471,775 | 9/1984 | Clair et al. | 128/207.15 |
| 4,495,948 | 1/1985 | Shapiro | 128/207.15 |
| 4,501,273 | 2/1985 | McGinnis | 128/207.15 |
| 4,565,194 | 1/1986 | Weerda et al. | 128/207.15 |

FOREIGN PATENT DOCUMENTS 62-8766 1/1987 Japan .

Primary Examiner—Edward M. Coven
Assistant Examiner—John P. Lacyk
Attorney, Agent, or Firm—Spencer & Frank

[57] ABSTRACT

A cuff pressure regulator for controlling the pressure in an annular, collapsible and inflatable bag-like cuff of a cuffed endotracheal tube inserted in a patient's trachea, while allowing superposition of the patient's ventilatory pressure variation on the cuff pressure. The regulator has a second chamber communicating with the inside of the cuff and a third chamber communicating with the inside of the tube inserted in the patient's trachea. A diaphragm portion of the partition between the second chamber and the third chamber is connected to a cuff pressure setter, so that the pressure in the second chamber is set at a desired level by the setter and controlled in response to the pressure variation in the third chamber.

11 Claims, 1 Drawing Sheet

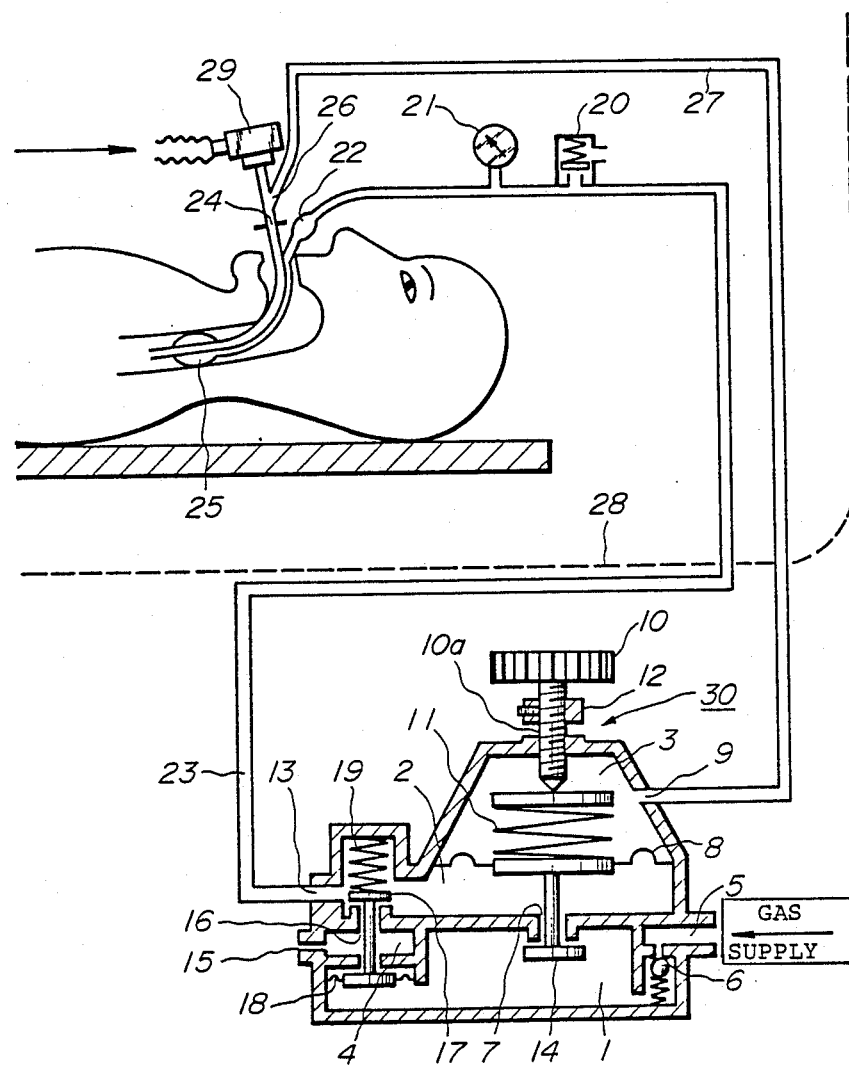

PRESSURE REGULATOR FOR CUFF OF ENDOTRACHEAL TUBE WITH SUPERPOSITION OF VENTILATING PRESSURE VARIATION

BACKGROUND OF THE INVENTION

1. Field of the Invention

This invention relates to a device which regulates the gas pressure within the annular collapsible and inflatable cuff of a cuffed endotracheal tube, which is a therapeutic apparatus for artificial ventilation and anesthesia. More particularly, the invention relates to a pressure regulator for a cuff of a cuffed endotracheal tube to maintain the intra-cuff gas pressure at a certain, but adjustable, safe and effective level despite variations in breathing pressure and/or variation of the ambient gas pressure. This device permits to automatically superimposing each breath-synchronized pressure variation on the basic intra-cuff pressure of the cuff being inflated along the endotracheal tube in the trachea so as to be set at an appropriate and constant pressure above the ambient pressure.

2. Description of the Prior Art

When a tube is inserted into the trachea of a patient for artificial ventilation or for inhalation of anesthetic gas (such a tube will be referred to as an "endotracheal tube", hereinafter), a ring-shaped hollow collapsible soft bag is usually attached as a cuff to the patient end of the endotracheal tube and the cuff is inflated by blowing a gas therein so as to hold the endotracheal tube in position while keeping airtight contact between the inside surface of the trachea and the endotracheal tube.

Previously, the so-called high-pressure cuff was used; namely the cuff is inflated by a comparatively high pressure gas. The high-pressure cuff has a shortcoming in that it may press against the internal wall of the trachea with a pressure so strong that it causes a disturbance in the trachea. Accordingly, low-pressure cuffs with less risk of causing a disturbance, which are inflatable by a large amount of low-pressure gas, have been used increasingly.

However, the low-pressure cuff has a shortcoming in that, due to its large surface area and the thin membrane forming the soft bag, the gas being inhaled through the endotracheal tube, such as an anesthetic laughing gas for general anesthesia, tends to diffuse into the cuff, resulting in an increased pressure within the cuff.

To overcome this shortcoming relating to the intra-cuff pressure (sometimes, referred to as "cuff pressure", hereinafter) of the conventional cuffed endotracheal tube, various cuff pressure regulators have been proposed, for instance by U.S. patent application Ser. No. 879,437 of the inventors, and others. Such cuff pressure regulators intend to maintain a constant cuff pressure regardless of occurrence of factors affecting the cuff pressure; such as variation of the tonicity (cough, excitement, etc.) and faccidity (relaxation) of the patient, variation of ambient pressure and ambient temperature.

When the cuff pressure is kept low with or without the cuff pressure regulator, if the positive pressure within the respiratory organs of the trachea increases intermittently, for instance as the result of artificial respiration, there is a risk that gases used for anesthesia and for artificial respiration can leak over the cuff because the pressure urging the cuff to the internal wall of the trachea is low. For similar reasons, there is a risk that when the pressure of the gas ventilated into the respiratory organs is high, such high pressure may act on the deeper side (towards the lungs) surface of the cuff in such a manner that the endotracheal tube being used may be pushed, transformed deviated and finally dropped out from the trachea.

To minimize such risks resulting from use of the low-pressure cuff, it is necessary to fasten the endotracheal tube by a suitable means or to increase the cuff pressure sufficiently to prevent the inadvertent drop out of the endotracheal tube and gas leakage. Consequently, the low-pressure cuff is not free from the risk of causing a disturbance on the internal wall of the trachea.

To prevent the above-mentioned gas leakage during artificial respiration and the inadvertent drop out of the endotracheal tube due to the pressure of the ventilated gas, methods for varying the cuff pressure with variation of the ventilatory pressure have been proposed. In the conventionally proposed methods, only when the pressure of the gas being ventilated into the respiratory organs is high, is a certain gas pressure added to an arbitrarily set basic cuff pressure. More particularly, the pressure of the respiratory organ is selectively added to the inhaling gas pressure toward the cuff, corresponding to the arbitrary set basic cuff pressure, through a diaphragm or a piston. However, the diaphragm is not durable because it is a thin membrane, while the piston involves problems such as resistance against movement and gas leakage. Further, even if the basic cuff pressure is set at a proper level beforehand, it cannot be used in a hyperbaric therapeutic chamber because the sudden ambient pressure change necessitates modification of the basic cuff pressure.

With respect to anesthesia using an endotracheal tube, there is a method in which gas with a pressure corresponding to the intermittent positive endotracheal pressure, caused by an artificial respirator or the like, is fed into the cuff of a cuffed endotracheal tube, so as to prevent leakage of the respiratory gas. When this method of preventing gas leakage is actually used, during the intermediate period between the intermittent gas supplied by the artificial respirator (lung ventilator) or the like, the endotracheal pressure is reduced to a level substantially equivalent to the ambient pressure, and the cuff pressure is similarly reduced to the same level as the ambient pressure, and the adhesion of the cuff to the internal surface of the trachea becomes insufficient. Thus, there is a serious risk in that, if phlegm, sputum, or vomitus is somehow brought to the trachea, they may be aspirated.

SUMMARY OF THE INVENTION

Therefore, an object of the present invention is to obviate the above-mentioned shortcomings and risks of the prior art by providing a novel pressure regulator for the cuff of a cuffed endotracheal tube in response to breath pressure variation. The pressure regulator of the invention, which is mountable on a conventional low-pressure cuff of a cuffed endotracheal tube, can deal with intermittent variations of endotracheal pressure by changing the cuff pressure in response to variation of the patient's ventilatory pressure, even if factors affecting the cuff pressure, such as variation of the ambient temperature or ambient pressure, occur during the use of the cuffed endotracheal tube.

To fulfil the above object, a pressure regulator for the cuff of a cuffed endotracheal tube has a first airtight chamber having a first port communicating with a pressurized gas source, and a second airtight chamber having a second port communicating with the inside of the cuff. The second airtight chamber is connected to the first airtight chamber through a first passage which is controllable by a pressure-regulating valve disposed therein. The pressure regulator of the invention also has a third airtight chamber having a third port communicating with a patient's breathing system including the endotracheal tube, and a fourth airtight chamber with an orifice open to the outside atmosphere. The third airtight chamber is separated from the second airtight chamber by a partition having a first diaphragm coupled to the pressure-regulating valve. The fourth airtight chamber is connected to the second airtight chamber through a second passage closable by a shut-off valve disposed therein. The fourth airtight chamber is separated from the first airtight chamber by a partition having a second diaphragm coupled to the shut-off valve.

Further, the pressure regulator of the invention has a cuff pressure setter coupled to the pressure-regulating valve so as to allow the setting of the operating characteristics of the pressure-regulating valve in such a manner that average gas pressure in the second airtight chamber is controlled at a desired cuff pressure level by the thus set pressure-regulating valve.

A gas is supplied from the first airtight chamber to the second airtight chamber through the pressure-regulating valve depending on a first differential pressure between the second airtight chamber and the third airtight chamber, while the gas is discharged to the outside atmosphere through the orifice under control of the shut-off valve in the second passage depending on a second differential pressure between the first airtight chamber and the fourth airtight chamber, so that gas pressure in the cuff becomes equivalent to the sum of the desired cuff pressure level and variation of the ventilatory pressure in the patient's breathing system.

The pressure regulator for the cuff of a cuffed endotracheal tube according to the invention considerably improves the therapeutic value of the cuffed endotracheal tube, because when the pressure regulator is connected to the cuff which is attached to a regular endotracheal tube or a regular tracheotomy tube, the airtight holding of such therapeutic tube in the trachea is remarkably enhanced. Furthermore, if the pressure regulator of the invention is attached to an artificial respirator (lung ventilator), an anesthetic apparatus, a hyperbaric (hypobaric) therapeutic apparatus, it improves the function of such therapeutic facilities to a noticeable extent.

BRIEF DESCRIPTION OF THE DRAWING

For a better understanding of the invention, reference is made to the accompanying single drawing.

The drawing shows a pressure regulator for the cuff of a cuffed endotracheal tube according to the present invention.

DESCRIPTION OF THE PREFERRED EMBODIMENT

In the single drawing, 1 is a first airtight chamber, 2 is a second airtight chamber, 3 is a third airtight chamber, 4 is a fourth airtight chamber, 5 is a first port, 6 is a one-way valve, 7 is a first passage, 8 is a first diaphragm, 9 is third port, 10 is a handle, 10a is an adjusting screw, 11 is a spring, 12 is a stopper, 13 is a second port, 14 is a pressure-regulating valve, 15 is an orifice, 16 is a second passage, 17 is a shut-off valve, 18 is a second diaphragm, 19 is a spring, 20 is a safety valve, 21 is a manometer, 22 is a pilot balloon, 23 is a small-diameter tube, 24 is a cuffed endotracheal tube, 25 is a cuff, 26 is a port, 27 is a pilot tube, 28 is a partition wall of a hyperbaric therapeutic chamber, 29 is a connector, and 30 is a cuff pressure setter.

The invention will now be described in detail by referring to an embodiment illustrated in the single drawing.

In the illustrated embodiment of the pressure regulator for the cuff of a cuffed endotracheal tube in response to ventilatory pressure variation according to the present invention, the essential portion of the pressure regulator consists of a combination of four air tight chambers; namely, a first airtight chamber 1, a second airtight chamber 2, a third airtight chamber 3, and a fourth airtight chamber 4. The first airtight chamber 1 has a first port 5 connected to a pressurized gas source (not shown). The illustrated example uses a one-way valve 6 disposed at the first port 5, so as to prevent reverse flow of the gas from the first airtight chamber 1 to the pressurized gas source. The one-way valve 6 may be formed by urging a ball, acting as a valve, against the port 5 by a spring.

The second airtight chamber 2 has a second port 13 which is connected, through a small-diameter tube 23, to a cuff 25 attached to the tip of an endotracheal tube 24. A safety valve 20 and a manometer 21 are connected to the small-diameter tube 23 for safety and pressure monitoring. A pilot balloon 22 is provided on the small-diameter tube 23 near that end thereof which is connected to the cuff 25. The third airtight chamber 3 has a third port 9 which is connected to the breathing system of the patient (not shown) or the cuffed endotracheal tube 24 through a pilot tube 27. The breathing system is, for instance, that of an anesthetic machine or a lung ventilator or the like, and it includes the endotracheal tube 24 and the patient's respiratory organs. In the illustrated embodiment, the third port 9 of the third airtight chamber 3 is connected to a port 26 of the endotracheal tube 24 through the pilot tube 27. The fourth airtight chamber 4 has an orifice 15 which allows gradual discharge of the gas from the pressure regulator to the outside atmosphere.

When the pressure regulator of the invention having the four airtight chambers 1–4 is used to control the gas pressure to inflate the cuff of an endotracheal tube in a patient in a hyperbaric therapeutic chamber as shown in the single drawing, the above-mentioned small-diameter tube 23 and the pilot tube 27 extend through the partition wall 28 of the hyperbaric therapeutic chamber in an airtight manner. Thus, the second airtight chamber 2 is properly connected to the cuff 25 in a high ambient pressure environment, and the third airtight chamber 3 is properly connected to the cuffed endotracheal tube 24 in the same environment.

The four airtight chambers 1–4, which are connected to the outside of the pressure regulator in the above-mentioned manner, are combined in the following manner.

The first airtight chamber 1 and the second airtight chamber 2 communicate each other through a first passage 7 which is bored through a partition wall therebetween. A pressure-regulating valve 14 is disposed in the first passage 7, so as to regulate the pressure of the gas in the second airtight chamber 2 by the opening and closing of the pressure-regulating valve 14. Thus, the pressurized gas from the first airtight chamber 1 is successively delivered through the second airtight chamber 2 and the small-diameter tube 23 until reaching the cuff 25, while receiving the pressure regulation at the pressure-regulating valve 14.

A flexible first diaphragm 8 defines a partition between the second airtight chamber 2 and the third airtight chamber 3. The first diaphragm 8 is coupled to the pressure-regulating valve 14 as shown in the single drawing, so that the degree of opening of the first passage 7 is controlled by a combination of the pressure-regulating valve 14 and the first diaphragm 8 depending on the first differential pressure between the second airtight chamber 2 and the third airtight chamber 3. A cuff pressure setter 30 is formed by a combination of an adjusting screw 10a extending through the wall of the third airtight chamber 3 and a spring 11 disposed between the inner end of the adjusting screw 10a and the first diaphragm 8. The outer end of the adjusting screw 10a is provided with a handle 10. The diaphragm side end of the spring 11 engages the joint portion of the pressure-regulating valve 14 with the first diaphragm 8, and the spring 11 is so compressed that it urges both the first diaphragm 8 and the pressure-regulating valve 14 in a direction to increase the opening of the first passage 7.

Thus, a desired basic cuff pressure is set by selecting the corresponding compression of the spring 11 through the turning of the handle 10. If the gas pressure in the second airtight chamber 2, i.e., the gas pressure in the cuff 25 delivered thereto through the small-diameter tube 23, is below the desired cuff pressure as determined by the angular position of the handle 10 or by the urging force of the spring 11 acting on both the first diaphragm 8 and the pressure regulating valve 14, the first differential pressure between the second airtight chamber 2 and the third airtight chamber 3 increases and causes the spring 11 to urge the pressure-regulating valve 14 downward so as to increase the opening of the first passage 7.

Accordingly, the pressurized gas from the pressurized gas source enters into the second airtight chamber 2 through the first airtight chamber 1, and further proceeds into the cuff 25 through the small-diameter tube 23, so as to increase the cuff pressure. When the gas pressure in the cuff 25 reaches the desired cuff pressure, the first differential pressure between the second airtight chamber 2 and the third airtight chamber 3 decreases, so as to allow the pressure-regulating valve 14 to move upward against the spring 11 until the first passage 7 is closed thereby. Thus, the gas pressure in the cuff 25 is maintained at the desired cuff pressure.

When the gas pressure in the cuff 25 is held at the desired cuff pressure as determined by the angular position of the handle 10 or the compression of the spring 11, if the gas pressure in the breathing system such as that in the endotracheal tube 24 increases and the increased ventilating gas pressure is delivered to the third airtight chamber 3 through the pilot tube 27, the first differential pressure across the first diaphragm 8 increases. Accordingly, the pressure-regulating valve 14 is pushed downward, and the first passage 7 opens again, and the pressurized gas enters into the second airtight chamber 2, so that the gas pressure in the cuff 25 surpasses the desired cuff pressure by an amount corresponding to the increment of the ventilating gas pressure. The increment of the ventilating gas pressure represents the corresponding increment of the gas pressure in the trachea in excess of the desired cuff pressure, and it also represents an increment of the patient's ventilatory pressure in excess of the desired cuff pressure.

Accordingly, when the pressure regulator of the invention is used for a patient in an environment where the ambient pressure varies considerably, such as in a hyperbaric therapeutic chamber, the variation of the patient's ventilatory pressure relative to the ambient pressure is extracted and delivered to the third airtight chamber 3 so as to cause an increment in the urging pressure on the first diaphragm 8. This means that a pressure variation which is a composite of the ventilatory (ventilating) pressure variation and the ambient pressure variation occurring in the hyperbaric therapeutic chamber or the like can be always added to the desired cuff pressure. In other words, when the ambient pressure and the ventilatory pressure increase, the pressure in the cuff 25 is raised by an amount equivalent to such increases, and on the contrary when the ambient pressure and the ventilatory pressure decrease, the pressure in the cuff 25 is reduced by an amount equivalent to such decreases.

Of the composite pressure variation of the ambient pressure and the ventilatory pressure, the ambient pressure variation is the same as that in the environment of the cuff 25, so that the ambient pressure component is cancelled, and in the end, only the ventilatory pressure variation relative to the ambient pressure is automatically added to the desired basic pressure of the cuff 25. Thus, the gas pressure in the cuff 25 always follows the variation of the gas pressure in the trachea, and the risk of leakage of the gas in the trachea, friction damage to the tracheal wall and the drop out of the endotracheal tube is eliminated.

A stopper 12 may be secured to the adjusting screw 10a as shown in the single drawing, so as to limit the turning of the handle 10 in the direction for increasing the desired cuff pressure. As a result, the handle 10 and the spring 11 are prevented from setting the desired cuff pressure at a level exceeding an allowable maximum urging pressure on the internal wall of the trachea.

The fourth airtight chamber 4 communicates with the second airtight chamber 2 through a second passage 16 bored through the partition therebetween, and a shut-off valve 17 is disposed in the second passage 16. The gas in the second airtight chamber 2 and in the cuff 25 communicating with the airtight chamber 2 through the small-diameter tube 23 is allowed to discharge gradually to the outside atmosphere through the second passage 16, the fourth airtight chamber 4 and the orifice 15. The fourth airtight chamber 4 is separated from the first airtight chamber 1 by a partition formed of a flexible second diaphragm 18 which is coupled to the shut-off valve 17 as shown in the single drawing. The second diaphragm 18 and the shut-off valve 17 are driven by a second differential pressure between the first airtight chamber 1 and the fourth airtight chamber 4.

The shut-off valve 17 has a valve rod extending toward the second diaphragm 18 through the fourth airtight chamber 4, while the opposite side of the shut-off valve 17 is urged by a spring 19 in a direction to close the second passage 16 from the second airtight chamber 2. Thus, the opening and closing of the second passage 16 by the shut-off valve 17 can be controlled by the pressure of the pressurized gas in the first airtight chamber 1.

The operation of the pressure regulator for the cuff of a cuffed endotracheal tube with superposition of the ventilatory pressure variation according to the present invention, whose construction has been described hereinbefore by referring to the single drawing, will be described now.

The pressure regulator of the illustrated structure for the cuff of an endotracheal tube with superposition of the ventilatory pressure variation according to the present invention not only holds the cuff pressure at a desired level, which level is preset through a proper means, but also extracts the ventilatory pressure in the trachea, where the cuffed endotracheal tube is inserted, and superimposes the difference of the breath pressure and the ambient pressure onto the cuff pressure, so that the risks of gas leakage through the gap at the cuff, friction damage to the internal wall of the trachea due to the transformation and deviation of the trachea and drop out of the cuffed endotracheal tube from the trachea are eliminated.

More particularly, when gas from the pressurized gas source is effectively supplied to the first airtight chamber 1 at a pressure above the desired cuff pressure, the second differential pressure between the first airtight chamber 1 and the fourth airtight chamber 4 acts to urge the second diaphragm 18 and the shut-off valve 17 in a direction to open the second passage 16. Thus, any excess gas in the cuff 25 can be gradually discharged to the outside atmosphere through the small-diameter tube 23, the second port 13, the second passage 16, the fourth airtight chamber 4, and the orifice 15.

Under such conditions, the first passage 7 is kept open until the pressure-regulating valve 14, which valve 14 is coupled to the first diaphragm 8 and adjusted for a desired cuff pressure by the cuff pressure setter 30, is urged against the passage 7. With the first passage 7 held open, the pressurized gas from the gas source flows into the second airtight chamber 2 through the first passage 7, and when the gas pressure in the second airtight chamber 2 reaches the desired cuff pressure set by the handle 10 of the cuff pressure setter 30, i.e., the basic cuff pressure or the allowable minimum limit pressure, an equilibrium condition is established, and the gas pressure in the cuff 25 is kept at the basic cuff pressure.

When the gas pressure in the cuff 25 is kept at the desired cuff pressure level, if the ventilatory pressure in the trachea intermittently increases in response to artificial respiration or the like, the conventional device is susceptible to disturbances such as the leakage of anesthetic gas or drop out of the endotracheal tube from the patient's trachea. However, with the pressure regulator of the invention, the risk of such disturbances is completely eliminated. More particularly, when the gas pressure in the breathing system including the endotracheal tube 24 increases with the increase of the ventilatory pressure, such increase of the breathing system gas pressure is introduced into the third airtight chamber 3 through the pilot pipe 27. The increment of the gas pressure in the third airtight gas chamber 3 acts as an addition to the urging pressure for the first diaphragm 8, which urging pressure is preset by the handle 10 of the cuff pressure setter 30.

Thus, the diaphragm 8 is pushed from the third airtight chamber 3 toward the first passage 7, and the above-mentioned pressure equilibrium to keep the preset cut pressure is broken. Through the now open first passage 7, the pressurized gas from the gas source enters into the second airtight chamber 2 through the first airtight chamber 1, and the gas pressure in the second airtight chamber 2 increases until it balances the increased gas pressure in the third airtight chamber 3 so as to establish a new pressure equilibrium. Then, the gas pressure in the cuff 25 which communicates with the second airtight chamber 2 increases to a level sufficient to counteract the increased ventilatory pressure in the trachea substantially without any delay. Thus, the risks of anesthetic gas leakage and the drop out of the endotracheal tube are completely eliminated, and the cuffed endotracheal tube 24 can be held in position within the patient's trachea, while keeping the airtight contact with the internal surface of the trachea with a proper pressure, regardless of the variation of the ventilatory pressure in the trachea.

On the contrary, when the gas pressure of the trachea decreases with the ventilatory pressure variation produced by artificial respiration or the like, the gas pressure in the third airtight chamber 3 also decreases due to its communication with the breathing system through the pilot tube 27, and the urging pressure on the first diaphragm 8 decreases accordingly. The first passage 7 is now blocked by the pressure-regulating valve 14 to interrupt the gas supply from the first airtight chamber 1 to the second airtight chamber 2. In the mean time, the gas in the second airtight chamber 2 gradually leaks to the outside through the second passage 16, the fourth airtight chamber 4, and the orifice 15, so that gas pressure of both the cuff 25 and the second airtight chamber 2, which has been raised by the preceding operation, now decreases to the present desired cuff pressure.

Thus, even when the ventilatory pressure in the trachea decreases, the risk of sucking vomitus into the lungs or the like is prevented. Although the cuff 25 airtightly engages the internal wall of the trachea for steady positioning, the pressure from the cuff 25 to the internal wall of the trachea is low, so that the blood flow through capillary vessels in the tracheal wall is not disturbed at all.

It is noted that, in the artificial respiration causing ventilating pressure variation in the trachea, as the gas pressure in the trachea intermittently increases, the above-mentioned increased cuff pressure presses the internal wall of the trachea and it may sometimes cause a temporary disturbance of the blood flow through the capillary vessels therein. However, since the gas pressure in the trachea periodically repeats the increase and decreases with the breathing rhythm, the cuff pressure decreases at each decrease of the ventilatory pressure in synchronism therewith, and the pressure on the internal wall of the trachea is periodically reduced, and the blood flow through the capillary vessels of the trachea wall also periodically recovers even if disturbed. Thus, with the pressure regulator for automatic regulation of the cuff pressure of the cuffed endotracheal tube according to the invention, the risk of causing any lasting disturbances by the artificial respiration or other operations accompanied with increased variation of ventilatory pressure in the trachea can be drastically reduced as compared with the prior art.

Next, the operation in the case of drop of the gas pressure in the first airtight chamber 1, due to exhaustion of the gas at the source, to a level below the preset pressure, which has been set by the operational pressure of the shut-off valve 17, will be explained. With such a low gas pressure at the first airtight chamber 1, the second differential pressure between the fourth airtight chamber 4 and the first airtight chamber 1 is decreased and the second diaphragm 18 is pressed downward by the spring 19, so as to block the second passage 16 by the shut-off valve 17, Thus, the gas in the cuff 25 is prevented from leaking through the orifice 15.

Although the pressure of the gas source is reduced, reverse flow from the first port 5 of first airtight chamber 1 to the gas source is prevented by the one-way valve 6. Since gas leakage is prevented at both the orifice 15 and the first port 5, the basic cuff pressure is maintained in the second airtight chamber 2. Thus, the first diaphragm 8, which separates the third airtight chamber 3 from the second airtight chamber 2, can be flexed toward the second airtight chamber 2 in response to and in synchronism with an increase of the gas pressure in the breathing system. Consequently, the function of the pressure regulator of the invention, namely, the function of delivering the composite gas pressure of the preset basic cuff pressure and the variation of the ventilating pressure in the trachea to the cuff 25 or the function of regulating the cuff pressure while superposing variation of the ventilatory pressure thereon, and can be ensured even if the gas pressure of the gas source is reduced or lost during the operation.

The pressure regulator of the invention can be used for controlling the cuff pressure of a cuffed endotracheal tube which is applied to a patient in a hyperbaric pressure therapeutic chamber. To prepare the pressure regulator of the invention for installation in the hyperbaric therapy or for application to a patient in the hyperbaric therapeutic chamber, it is sufficient to set the basic cuff pressure at a suitable desired level by the cuff pressure setter 30 before the start of the therapy. No other special adjustments are necessary until the end of the therapy in the hyperbaric therapeutic chamber. Nevertheless, the above-mentioned cuff pressure control while superposing the ventilating pressure variation on the basic cuff pressure in synchronism with the gas pressure variation in the trachea due to the patient's breathing or artificial respiration is effected in the hyperbaric therapeutic chamber. In short, the pressure regulator of the invention can be used for patients in the hyperbaric therapeutic chamber without any special adjustments.

As explained before, when the pressure regulator of the invention is placed outside the hyperbaric chamber, the small-diameter tube 23 and the pilot tube 27 can be connected to a cuffed endotracheal tube 24 used therein by airtightly extending them through the partition wall 28 of the high-pressure chamber, which partition wall 28 is shown by the dash-line in the single drawing. In this case, a cuff pressure of the cuffed endotracheal tube 24 used in the hyperbaric chamber can be arbitrarily controlled from the outside of such chamber even during the hyperbaric therapy.

As described in detail in the foregoing, the pressure regulator according to the invention, when connected to the cuff of a cuffed endotracheal tube applied to a patient, always maintains the pressure of the cuff at the sum of an arbitrarily set basic cuff pressure and variation of gas pressure in the patient's trachea relative to his ambient pressure, the variation being superposed on the basic cuff pressure, by supplying a pressurized gas from a gas source to the regulator at a pressure higher than the maximum cuff pressure necessary for the cuffed endotracheal tube, gradually discharging the gas from the regulator to the outside atmosphere through an orifice, and controlling the gas supply and the gas discharge through opening and closing of those valves which are specifically provided for such gas flow control. Accordingly, the pressure regulator of the invention can control the gas pressure in the cuff of such cuffed endotracheal tube at optimum value under any foreseeable conditions for actual time.

Accordingly, the pressure regulator for the cuff of a cuffed endotracheal tube with superposition of a ventilating pressure variation according to the invention eliminates the risk of gas leakage in the trachea or drop out of the endotracheal tube from a patient during inhalation of anesthetic operation or artificial respiration, and the basic cuff pressure can be set at a minimum necessary level, so that disturbance caused on the internal wall of the patient's trachea can be drastically reduced as compared with the case of conventional regulators. If the pressure regulator of the invention is used, artificial respiration can be properly effected in a hyperbaric therapeutic chamber when necessary, despite the fact that a sudden change in the ambient pressure may occur in the course of hyperbaric therapy. The pressure regulator of the invention prevents gas leakage in the trachea and aspiration of vomit and secretion from the cuff periphery, so that optimum function of the cuffed endotracheal tube can be maintained and fully utilized.

Furthermore, the pressure regulator of the invention can be used for a patient in a hyperbaric therapeutic chamber simply by setting a desired cuff pressure before starting the therapy. Even if the pressure in the therapeutic chamber varies during the therapy, readjustment of the desired cuff pressure is not necessary, and the above-mentioned optimum cuff pressure regulation can be always maintained.

Although the invention has been described by referring to a preferred embodiment, numerous modifications are possible in parts and construction without departing from the scope of the invention as hereinafter claimed.

What is claimed is:

1. A cuff pressure regulator for controlling the pressure applied by the cuff of an endotracheal tube to the inner wall of a patient's trachea, comprising
   a first chamber including means for the connection thereof to a pressurized gas supply source;
   a second chamber adapted to be connected to the cuff of the endotracheal tube disposed within the patient's trachea;
   a third chamber adapted to be connected to said endotracheal tube, said third chamber being maintained at the same pressure as that within the endotracheal tube;
   a fourth chamber having an orifice connecting said fourth chamber to the outside of said regulator and a passage connecting said fourth chamber to said second chamber;
   pressure regulating valve means interposed between said first and second chambers for controlling the flow of gas therebetween;
   valve driving means having a partition including a first diaphragm separating said second and third chambers and being connected to said pressure regulating valve means, said valve driving means displacing said pressure regulating valve means in response to a pressure difference between said second and third chambers, said pressure regulating valve means being opened by said valve driving means when the pressure in said second chamber is lower than the sum of a predetermined basic cuff pressure and the pressure within the endotracheal tube, and closed when the pressure in said second chamber reaches the sum of said predetermined basic cuff pressure and the pressure within said endotracheal tube; and pressure setting means connected to said valve driving means for setting said predetermined basic cuff pressure, whereby gas having a pressure higher than the sum of said predetermined basic cuff pressure and the pressure within said endotracheal tube is supplied from the pressurized gas supply source to said first chamber.

2. A cuff pressure regulator according to claim 1 which further comprises shut-off valve means interposed between said second and fourth chambers for controlling the flow of gas therebetween, said shut off valve means including shut-off valve controlling means having
- a partition including a second diaphragm separating said first and fourth chambers; and
- a spring means exerting a pressure on said shut-off valve means to prevent the flow of gas from said second chamber to said orifice when the pressure in said first chamber falls below the sum of said predetermined basic cuff pressure and the pressure within said endotracheal tube, said shut-off valve controlling means controlling the flow of gas from said second chamber through the orifice in said fourth chamber whereby the gas is allowed to discharge through said orifice when the cuff pressure is being maintained at the sum of said predetermined basic cuff pressure and the pressure within said endotracheal tube, and discharge of gas through said orifice being prevented when the gas pressure in said first chamber falls below the sum of said predetermined basic cuff pressure and the pressure within said endotracheal tube.

3. A cuff pressure regulator for controlling the pressure applied by the cuff of an endotracheal tube to the inner wall of a patient's trachea, comprising
- a first chamber including means for the connection thereof to a pressurized gas supply source;
- a second chamber adapted to be connected to the cuff of the endotracheal tube disposed within the patient's trachea;
- a third chamber adapted to be connected to said endotracheal tube, said third chamber being maintained at the same pressure as that within the endotracheal tube;
- a fourth chamber having an orifice connecting said fourth chamber to the outside of said regulator and a passage connecting said fourth chamber to said second chamber;
- pressure regulating valve means interposed between said first and second chambers for controlling the flow of gas therebetween;
- valve driving means having a partition including a first diaphragm separating said second and third chambers and being connected to said pressure regulating valve means, said valve driving means displacing said pressure regulating valve means in response to a pressure difference between said second and third chambers, said pressure regulating valve means being opened by said valve driving means when the pressure in said second chamber is lower than the sum of a predetermined basic cuff pressure and the pressure within the endotracheal tube, and closed when the pressure in said second chamber reaches the sum of said predetermined basic cuff pressure and the pressure within said endotracheal tube;
- pressure setting means connected to said valve driving means for setting said predetermined basic cuff pressure, whereby gas having a pressure higher than the sum of said predetermined basic cuff pressure and the pressure within said endotracheal tube is supplied from the pressurized gas supply source to said first chamber; and
- shut-off valve means interposed between said second and fourth chambers for controlling the flow of gas therebetween, said shut-off valve means including shut-off valve controlling means having a partition including a second diaphragm separating said first and fourth chambers, said shut-off valve controlling means controlling the flow of gas from said second chamber through the orifice in said fourth chamber whereby the gas is allowed to slowly discharge through said orifice when the cuff pressure is being maintained at the sum of said predetermined basic cuff pressure and the pressure within said endotracheal tube, discharge of gas through said orifice being prevented when the gap pressure in said first chamber falls below the sum of said predetermined basic cuff pressure and the pressure within said endotracheal tube.

4. A cuff pressure regulator according to claim 3 which further comprises a one-way valve interposed between said first chamber and the pressurized gas supply source, said one-way valve allowing gas flow only from said gas supply source to said first chamber and inhibiting gas flow in the opposite direction.

5. A cuff pressure regulator according to claim 4 wherein said shut-off valve controlling means further comprises a spring means exerting a pressure on said shut-off valve means to prevent the flow of gas from said second chamber to said orifice when the pressure in said first chamber falls below the sum of said predetermined basic cuff pressure and the pressure within said endotracheal tube.

6. A cuff pressure regulator according to claim 3 wherein said pressure setting means comprises an adjusting screw and a spring interposed between said adjusting screw and said pressure regulating valve means, said spring urging said pressure regulating valve in a direction to permit flow of gas between said first and second chambers.

7. A cuff pressure regulator according to claim 4 wherein said pressure setting means comprises an adjusting screw and a spring interposed between said adjusting screw and said pressure regulating valve means, said spring urging said pressure regulating valve in a direction to permit flow of gas between said first and second chambers.

8. A cuff pressure regulator according to claim 5 wherein said pressure setting means comprises an adjusting screw and a spring interposed between said adjusting screw and said pressure regulating valve means, said spring urging said pressure regulating valve in a direction to permit flow of gas between said first and second chambers.

9. A cuff pressure regulator according to claim 6 wherein said pressure setting means includes a stopper secured to said adjusting screw, said stopper limiting the urging of said spring in said direction.

10. A cuff pressure regulator according to claim 7 wherein said pressure setting means includes a stopper secured to said adjusting screw, said stopper limiting the urging of said spring in said direction.

11. A cuff pressure regulator according to claim 8 wherein said pressure setting means includes a stopper secured to said adjusting screw, said stopper limiting the urging of said spring in said direction.

* * * * *